US008650958B2

(12) United States Patent
Fetzer et al.

(10) Patent No.: US 8,650,958 B2
(45) Date of Patent: Feb. 18, 2014

(54) THIN-FILM ULTRASONIC PROBE HAVING A FLEXIBLE MEMBRANE

(75) Inventors: Barry A. Fetzer, Renton, WA (US); James C. Kennedy, Renton, WA (US); Thomas E. Riechers, Bonney Lake, WA (US)

(73) Assignee: The Boeing Company, Chicago, IL (US)

( * ) Notice: Subject to any disclaimer, the term of this patent is extended or adjusted under 35 U.S.C. 154(b) by 2038 days.

(21) Appl. No.: 11/345,905

(22) Filed: Feb. 2, 2006

(65) Prior Publication Data

US 2007/0175282 A1    Aug. 2, 2007

(51) Int. Cl.
*G01N 29/28*    (2006.01)

(52) U.S. Cl.
USPC .......................................................... 73/644

(58) Field of Classification Search
USPC .................................. 73/628, 649, 644, 636
See application file for complete search history.

(56) References Cited

U.S. PATENT DOCUMENTS

| | | | | |
|---|---|---|---|---|
| 2,992,553 | A * | 7/1961 | Joy | 73/636 |
| 3,960,005 | A * | 6/1976 | Vezina | 73/614 |
| 3,962,908 | A * | 6/1976 | Joy | 73/636 |
| 4,421,118 | A * | 12/1983 | Dow et al. | 600/446 |
| 4,662,215 | A * | 5/1987 | Eckert | 73/61.75 |
| 4,699,150 | A * | 10/1987 | Kawabuchi et al. | 600/446 |
| 5,675,084 | A * | 10/1997 | Goedecke | 73/623 |
| 6,722,202 | B1 | 4/2004 | Kennedy et al. | |
| 7,284,434 | B1 * | 10/2007 | Fleming | 73/644 |
| 7,330,683 | B2 * | 2/2008 | Matsuzaki | 399/279 |
| 2003/0013968 | A1 * | 1/2003 | Fjield et al. | 600/459 |
| 2004/0003664 | A1 * | 1/2004 | Ishikawa et al. | 73/644 |
| 2006/0065055 | A1 * | 3/2006 | Barshinger et al. | 73/609 |
| 2007/0175282 | A1 * | 8/2007 | Fetzer et al. | 73/649 |
| 2008/0236288 | A1 * | 10/2008 | Nieters et al. | 73/644 |

OTHER PUBLICATIONS

U.S. Appl. No. 10/943,088, filed Sep. 16, 2004, Georgeson et al.
U.S. Appl. No. 10/943,135, filed Sep. 16, 2004, Georgeson et al.
Innovation in NDT™ brochure, p. 19, printed Aug. 2004.
Innovation in NDT™ "Olympus NDT—Phased-Array Probes—Immersion Probes," www.rd-tech.com/paprobes_immersion.html.
Innovation in NDT™ "Olympus NDT—Phased Array Probes—Contact Probes," www.rd-tech.com/paprobes_contact.html.
NDT Solutions Ltd, "Ultrasonic Wheel Probes," www.ndtsolutions.com/wheel.htm.
Innovation in NDT™ "Olympus NDT—Phased-Array Probes—Angle Beam Probes with External Wedges," www.rd-tech.com/paprobes_anglebeam.html.

(Continued)

*Primary Examiner* — Peter Macchiarolo
*Assistant Examiner* — Samir M Shah (57) ABSTRACT

An ultrasonic probe for examining an item. The probe includes a body having a contact surface adapted for contacting the item when being examined and an ultrasonic transducer attached to the body and spaced from the contact surface. The probe further includes a spacer positioned in the body between the transducer and the contact surface for spacing the transducer from the item when being examined. The spacer includes a coupling surface facing the item when being examined and a transducer surface facing the transducer. The probe also includes a fluid outlet positioned adjacent the coupling surface of the spacer for delivering coupling fluid to the coupling surface as a film so that the coupling fluid tends to maintain contact with the spacer due to surface tension after the fluid is delivered through the outlet.

13 Claims, 6 Drawing Sheets

(56) References Cited

OTHER PUBLICATIONS

Innovation in NDT™ "Olympus NDT—Phased-Array Probes—What are Phased-Array Probes?," www.rd-tech.com/paprobes.html.
Innovation in NDT™ "Olympus NDT—Phased-Array Probes—Angle Beam Probes with Internal Wedges," www.rd-tech.com/paprobes_anglebeamint.html.
Innovation in NDT™ "Contact Ultrasonic Transducers," www.panametrics-ndt.com/ndt/ndt_transducers/contact/index.html.
Innovation in NDT™ "Ultrasonic Couplants," www.panametrics-ndt.com/ndt/ndt_technology/ultrasonic_couplants.html.
Innovation in NDT™ "Olympus NDT—Angle Beam Testing and 0 Degree Testing," www.rd-tech.com/tech_ultra_angle.html.
Innovation in NDT™"Olympus NDT—Aqualene Couplant," www.rd-tech.com/couplant.html.

* cited by examiner

THIN-FILM ULTRASONIC PROBE HAVING A FLEXIBLE MEMBRANE

BACKGROUND OF THE INVENTION

The present invention relates to examination probes and, more particularly, to thin-film ultrasonic probes.

An ultrasonic probe is used to examine items such as manufactured parts by transmitting ultrasonic signals to the item and measuring a reflected signal returned by the item to the probe. Conventional probes typically include a transducer having a single crystal that creates the outgoing ultrasonic signals and measures the signals returned to the transducer. To facilitate the transmission of signals between conventional probes and the item being examined, the item is often wetted with water where the probe will be moved. The ultrasonic signals more easily transfer from the transducer to the item by way of the water disposed between the probe and the item. Without such a coupling fluid, some of the signals leaving the transducer would not reach the item, instead being reflected back to the transducer by a gap of air that may exist between the probe and the item. Ultrasonic signals reflect at interfaces where the density of transfer media decreases sufficiently, such as the case between a solid such as metal and a gas such as air, because the signals propagate through the path of least resistance, which may include remaining in the denser media. Such unwanted reflections confuse item examination by causing confusion with reflections from within the item. Further, without a coupling fluid, some of the signals that do make it to the item may not return to the transducer as intended because they are reflected back into the item at the previously mentioned air gap. In one conventional method, a spray bottle is used to repeatedly spray water on the item ahead of the probe as the probe is moved along a surface of the item.

The conventional method of frequently applying water to the item using external devices such as a spray bottle is tedious and hinders the examination process. For example, because the water must be applied as the probe is moved and the existence of a sufficient and consistent amount of water between the probe and the item cannot be ensured, a substantial amount of water must be applied and the probe must be moved slowly.

When examining items, it is often desired to examine edges of the item. However, when a portion of conventional probes is moved over an edge, any coupling fluid that was disposed beneath the portion of the probe moved beyond the edge falls over the edge leaving no coupling fluid adjacent that portion. When coupling fluid is absent from the over-the-edge portion of the probe, the fluid between the probe and the item adjacent the edge will tend to also flow over the edge. When this happens, the probe is unable to accurately determine characteristics of the item adjacent the edge. For example, the conventional probe cannot distinguish whether a signal reflected back to the transducer from air below the probe indicates the signal was reflected from air beneath the probe beyond an item edge or air caused by a lack of coupling fluid between the probe and the item because the fluid there flowed over the edge.

Further, it is difficult to accurately determine characteristics of item edges using a single crystal transducer. Depending on the positioning of the crystal on the probe, a good amount of the probe could be moved over the edge without the transducer knowing. Also, when the single crystal transducer does register that there is no item below the part, it is difficult to accurately identify the location of the crossed edge. In addition, with a single crystal transducer, the transducer may prematurely determine that the crystal is over an edge when the signal path has actually encountered an area over the item where the coupling fluid already began flowing over the edge as described. A probe and method of using it are needed that improve the coupling of probes to items being examined allowing reliable, expedient, and accurate evaluation of item characteristics including at their edges.

BRIEF SUMMARY OF THE INVENTION

The present invention relates to an ultrasonic probe for examining a part. The probe includes a body having a contact surface adapted for contacting the part when being examined and an ultrasonic transducer attached to the body and spaced from the contact surface. The probe further includes a spacer positioned in the body between the transducer and the contact surface for spacing the transducer from the part when being examined. The spacer includes a coupling surface facing the part when being examined and a transducer surface facing the transducer. The probe also includes a fluid outlet positioned adjacent the coupling surface of the spacer for delivering coupling fluid to the coupling surface as a film so that the coupling fluid tends to maintain contact with the spacer due to surface tension after the fluid is delivered through the outlet.

In another aspect, the present invention relates to a method for examining a part using an ultrasonic probe. The probe includes a body having a contact surface and a coupling fluid channel extending between a coupling fluid inlet and a coupling fluid outlet in the contact surface. The probe further includes a spacer including delay fluid disposed in a chamber of the body and a membrane adjacent the contact surface sealing the delay fluid inside the chamber and forming a coupling surface and an ultrasonic transducer connected to the body adjacent the spacer. The method includes positioning the contact surface of the probe body in contact with a contact surface of the part and delivering coupling fluid to the coupling surface of the spacer by way of the fluid channel to form a film of the coupling fluid on the coupling surface. The method further includes producing ultrasonic signals using the transducer and propagating the signals through the spacer and to the part. The method also includes moving the probe along the contact surface of the part and determining characteristics of the part based on ultrasonic signals reflected from the part back to the transducer.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE INVENTION

Figure 1:
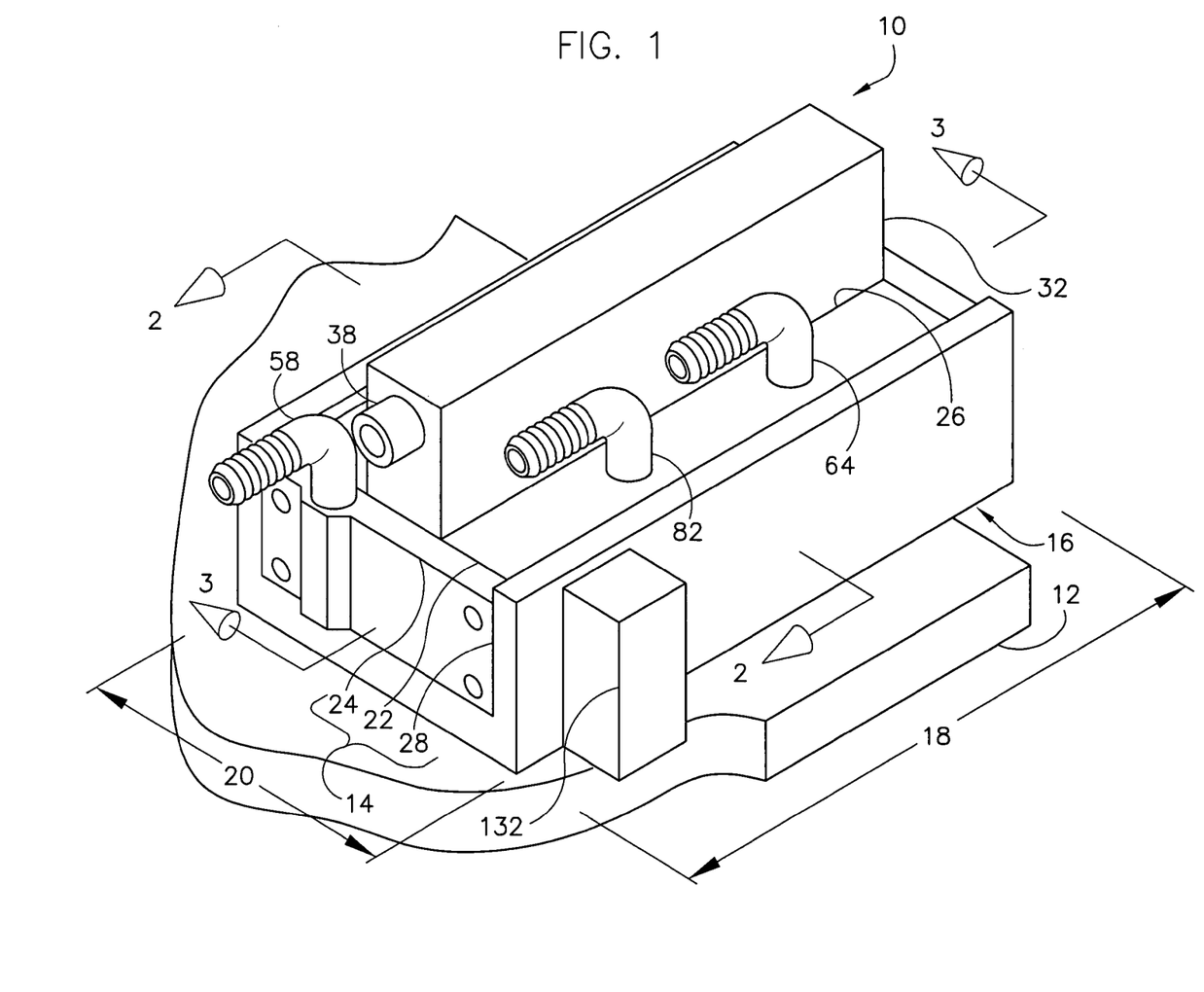
FIG. 1 is a perspective of an ultrasonic probe according to the present invention and a part being examined by the probe.
Figure 2:
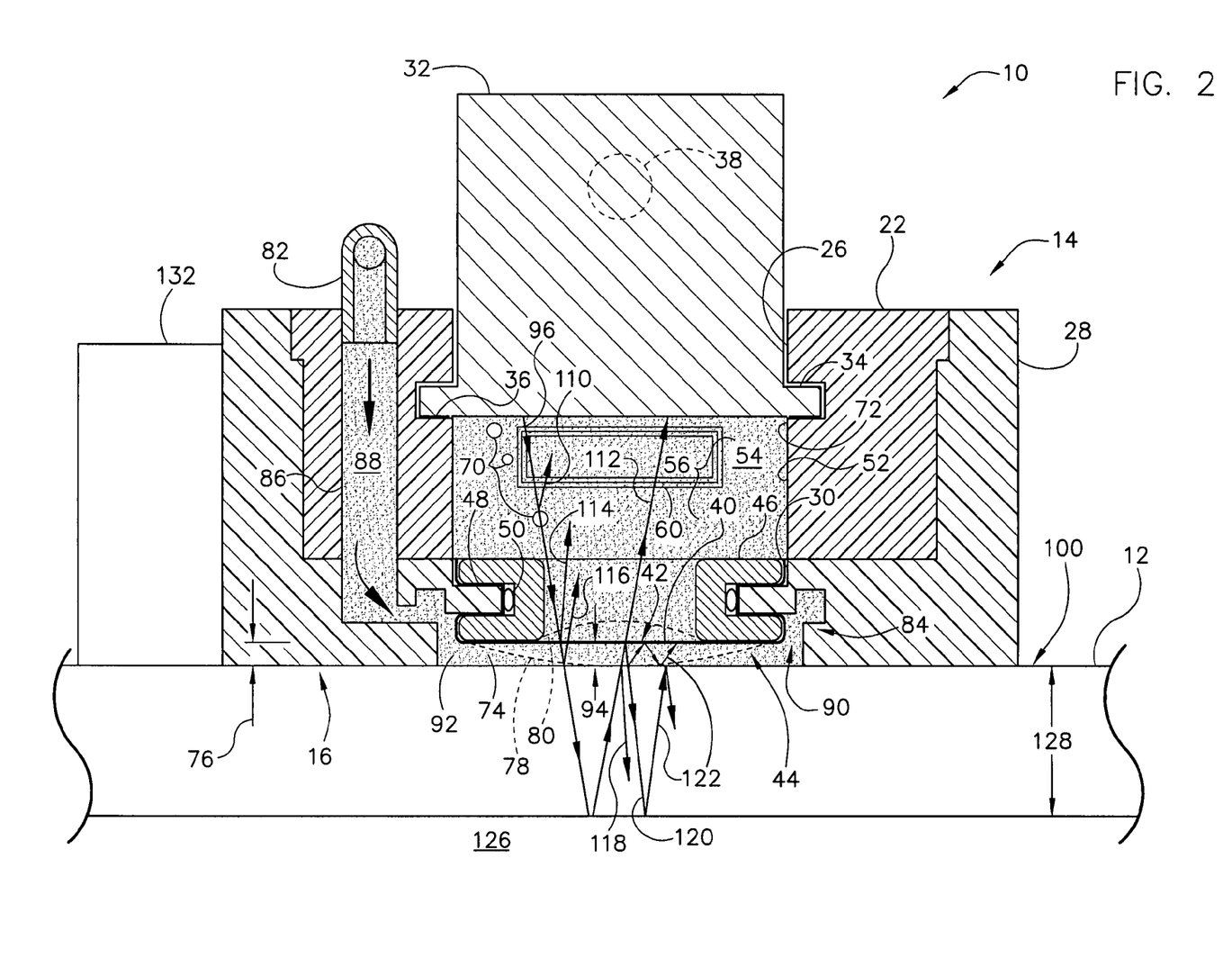
FIG. 2 is a cross section of the probe and the part taken along line 2-2 of FIG. 1.
Figure 3:
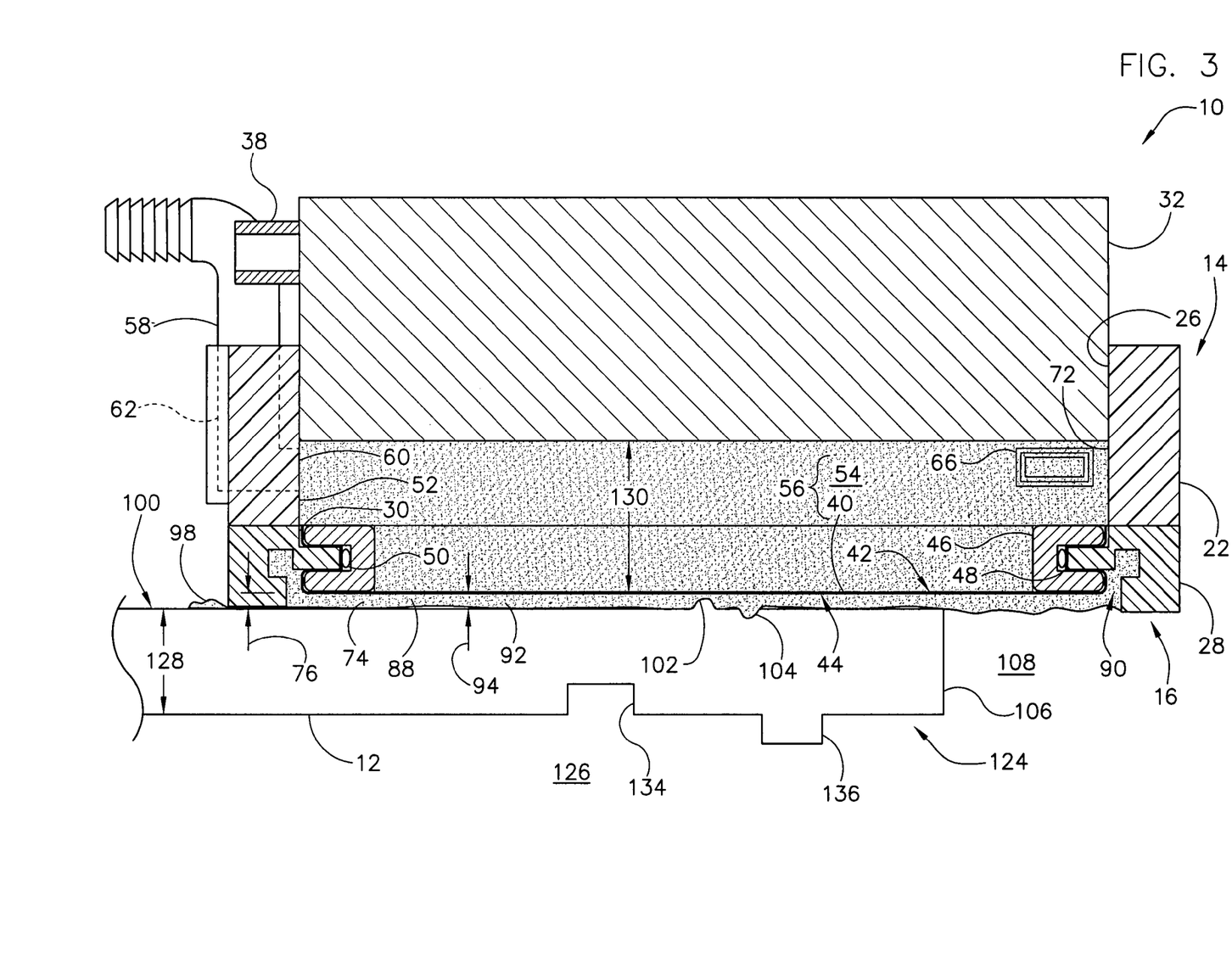
FIG. 3 is a cross section of the probe and the part taken along line 3-3 of FIG. 1.

Referring to the figures, and more particularly to FIG. 1, an ultrasonic probe according to the present invention is designated in its entirety by reference number 10. The probe 10 is used to examine an item such as a manufactured part 12. Although the probe 10 may be used to examine other parts 12 without departing from the scope of the present invention, in one embodiment the probe is used to examine parts of an aircraft or other vehicle. The probe 10 includes a body 14 having a contact surface 16 adapted for contacting the part 12 during examination. Although the body 14 may have other lengths 18 without departing from the scope of the present invention, in one embodiment the body has a length of between about 4.7 inches and about 5.0 inches. Although the body 14 may have other widths 20 without departing from the scope of the present invention, in one embodiment the body has a width of between about 2.8 inches and about 3.2 inches. In one embodiment, the body 14 is made of a low-friction material, such as a polymer, so the probe 10 can easily slide across the part 12. Although the body 14 may be made of other materials without departing from the scope of the present invention, in a particular embodiment the body 14 is made of nylon. The body 14 has opposite sides 22 and opposite ends 24 that form a cavity 26 between them. The body 14 may further include a generally c-shaped shoe or base 28 partially encasing the sides 22 and the ends 24. As shown in FIGS. 2 and 3, the base 28 includes an opening 30 corresponding to the cavity 26. Any combination of the sides 22, the ends 24, and the base 28 may be formed integrally. For example, the sides 22 and the base 28 may be formed as a unitary piece.

The probe 10 further includes one or more transducers 32 attached to the body 14 and positioned in the cavity 26. The transducer 32 may be connected to the body 14 in various ways without departing from the scope of the present invention. For example, as shown in FIG. 2, the transducer 32 may include a lip 34 on opposite sides of the transducer that engage slots 36 of the sides 22 of the body 14 when the probe 10 is assembled. The transducer 32 produces signals with which the part 12 is examined. The signals are transmitted from the transducer 32, through the part 12, and back through the part to the transducer. The transducer 32 includes or is configured for connection to a controller (not shown) and a power source (not shown). For example, the transducer 32 may include a control port 38 for connecting the transducer to an external controller. The controller manages transducer 32 signal output and interprets signals received by the transducer. Although other controllers may be used without departing from the scope of the present invention, in one embodiment the controller is an omniscan controller, available from Olympus-NDT, Inc., of Waltham, Mass.

The transducer 32 may include one or more crystals (not shown) producing the ultrasonic signals. As will be apparent by those skilled in the art, the crystals produce ultrasonic signals by oscillating in response to voltage input to them. The crystals also sense the signals that reflect back to the transducer 32 from the part 12 or otherwise for determining part characteristics, such as size, shape, and interior imperfections (not shown). Examples of interior imperfections the transducer 32 may sense include delaminations, or unwanted separations between layers (not shown) of the part 12, and porosity outside of a predetermined range. In one embodiment, the transducer 32 includes an array or matrix of crystals (not shown in detail). Although such a transducer 32 array may include other numbers of crystals, in one embodiment the array contains between 16 and 128 crystals. In a particular embodiment, the array includes 64 crystals. Although other transducers 32 may be used without departing from the scope of the present invention, in one embodiment the transducer is a phased-array transducer, available from Olympus-NDT, Inc., of Waltham, Mass.

Figure 4:
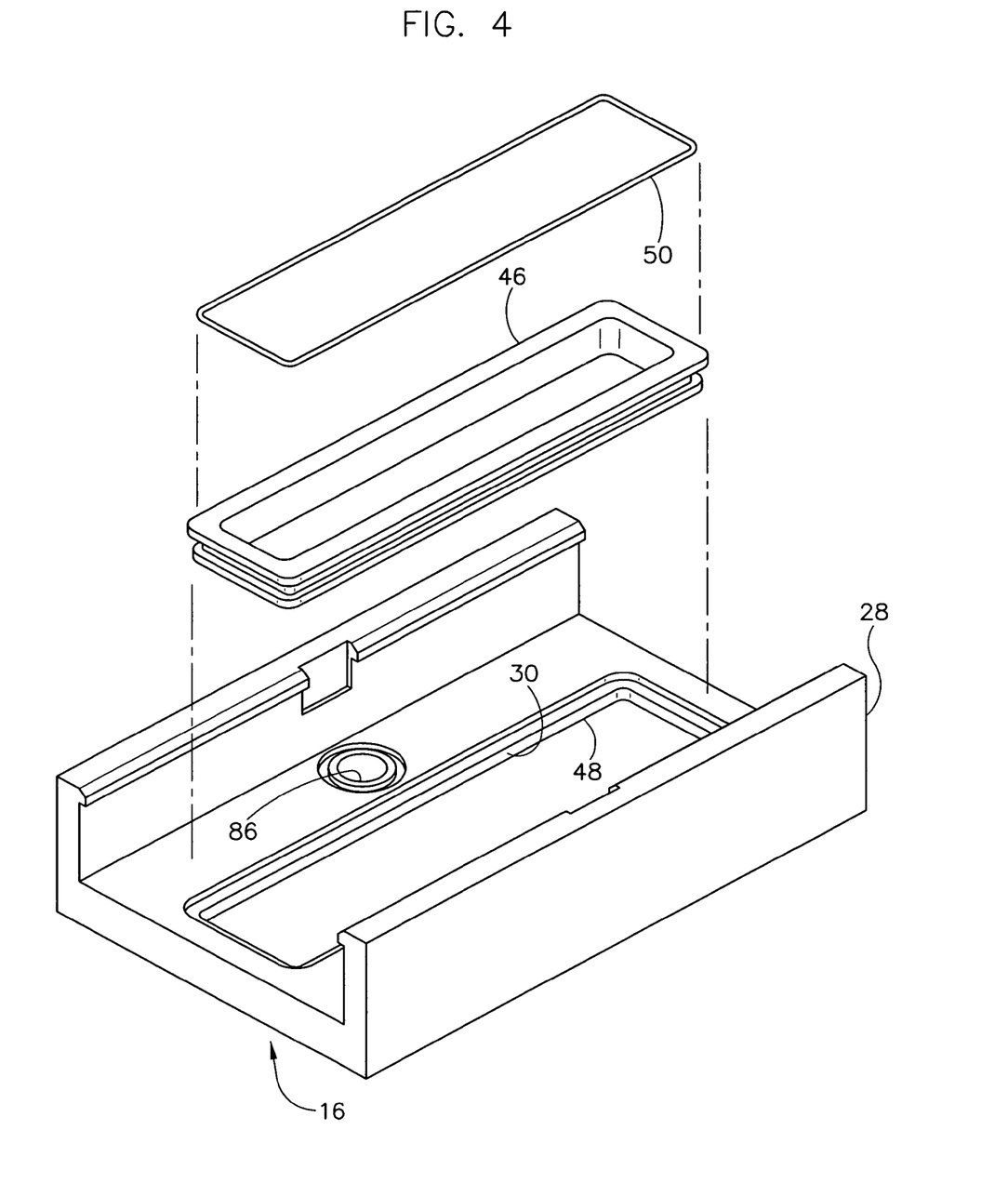
FIG. 4 is a perspective of a base, an insert, and an o-ring of the probe.

The probe 10 further includes a flexible membrane 40 mounted on the body 14 adjacent and spaced from the contact surface 16. The membrane 40 includes an upper or chamber surface 42 and a lower or coupling surface 44. Although the membrane 40 may be made of other materials without departing from the scope of the present invention, in one embodiment the membrane is made of latex rubber. The membrane 40 may be connected to the body 14 in various ways without departing from the scope of the present invention. For example, the probe 10 may include a gasket or insert 46 that seals the membrane 40 against sides of the base opening 30. In one embodiment, the insert 46 is generally c-shaped for receiving a flange 48 of the base 28 adjacent the opening 30. The probe 10 may also include a sealing component such as an o-ring 50 positioned between the insert 46 and the flange 48 when the probe is assembled to increase the strength of the seal between the membrane 40 and the body 14. The o-ring 50 may be secured to the insert 46 to prevent relative movement between them. For example, the o-ring 50 may be glued to the insert 46. The insert 46 and o-ring 50 are positioned in the opening 30 of the base 28 as shown in FIG. 4.

Figure 5:
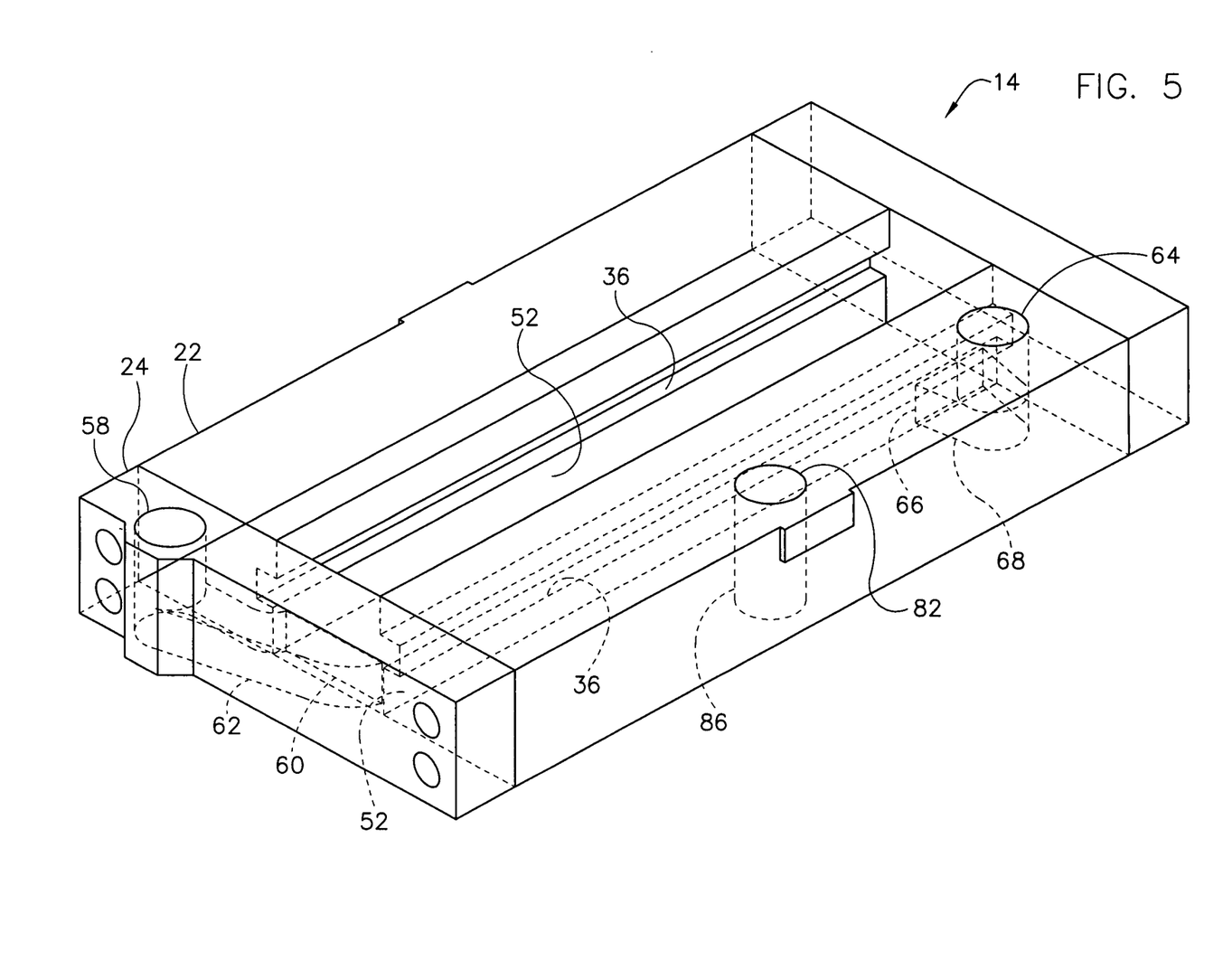
FIG. 5 is a perspective of opposite sides and opposite ends of the probe.

The membrane 40, the body sides 22, the body ends 24, and the transducer 32 form a chamber 52. During operation of the probe 10, delay fluid 54 is circulated through the chamber 52. The delay fluid 54 and membrane 40 constitute a delay line or spacer 56 through which the transducer 32 signals are transmitted on their way to and from the part 12 when the probe 10 is used. Although other delay fluids 54 may be used without departing from the scope of the present invention, in one embodiment the delay fluid is water. As shown in FIG. 3, the body 14 further includes a delay fluid inlet 58 and a chamber inlet 60 connected by a delay fluid feed channel 62. The delay fluid inlet 58 is configured to be connected to an external delay fluid source (not shown). As shown in FIG. 5, the body 14 also includes a delay fluid outlet 64 and a chamber outlet 66 connected by a delay fluid exit channel 68. During operation of the probe 10, delay fluid 54 is delivered to the chamber 52 by way of the delay fluid feed channel 62 and from the chamber by way of the delay fluid exit channel 68. The delay fluid outlet 64 may be connected to a reservoir or drain (not shown) or connected to the delay fluid source for recirculation to the chamber 52. Because of the shape of the body 14, including multiple internal channels, some of which may change directions, it may be advantageous to fabricate the body using a rapid prototyping method. For example, any or all of the body 14 may be made using selective laser sintering. In selective laser sintering, thermoplastic powder is sintered or melted by a laser in select locations to form the part.

It is important to keep the delay fluid 54 substantially free of air pockets and air bubbles during probe 10 use. Unwanted air 70 (shown in FIG. 2) in the delay fluid 54 interferes with the propagation of transducer 32 signals to and from the part 12. Continuous or intermittent circulation of delay fluid 54 through the chamber 52 keeps unwanted air 70 from forming and staying in the chamber by moving the fluid and any such air out through the chamber outlet 66. Further, as shown in FIG. 3, the chamber inlet 60 and/or the chamber outlet 66 may be positioned adjacent a top 72 of the chamber. Circulating delay fluid 54 adjacent the top 72 of the chamber 52 reduces unwanted spacer 56 air 70 because bubbles tend to cavitate and float there.

When the membrane 40 is in an unflexed position, its coupling surface 44 is offset from the contact surface 16 of the body 14 to form a recess 74. Although the recess 74 may have other depths 76 when the membrane 40 is unflexed without departing from the scope of the present invention, in one embodiment the recess has a depth of between about 0.04 inch and about 0.06 inch when the membrane is unflexed. In one embodiment, when the membrane 40 is flexed to a convex position 78 (shown in FIG. 2), the recess depth 76 has a minimum of between about 0.000 inch and about 0.06 inch and when the membrane is flexed to a concave position 80, the recess depth 76 has a minimum of between about 0.05 inch and about 0.08 inch.

The probe 10 further includes a coupling fluid inlet 82 and a coupling fluid outlet 84 connected by a coupling fluid channel 86. The coupling fluid inlet 82 is configured to be connected to an external coupling fluid source (not shown). The probe 10 may include a single coupling fluid outlet 84 distributed around a portion of or all of the recess 74 or may include multiple coupling fluid outlets (not shown) spaced around the recess. The coupling fluid outlet 84 may be positioned in or adjacent the contact surface 16 of the body 14 and is configured so coupling fluid 88 is delivered to the recess 74 so it contacts the coupling surface 44 of the spacer 56.

Figure 6:
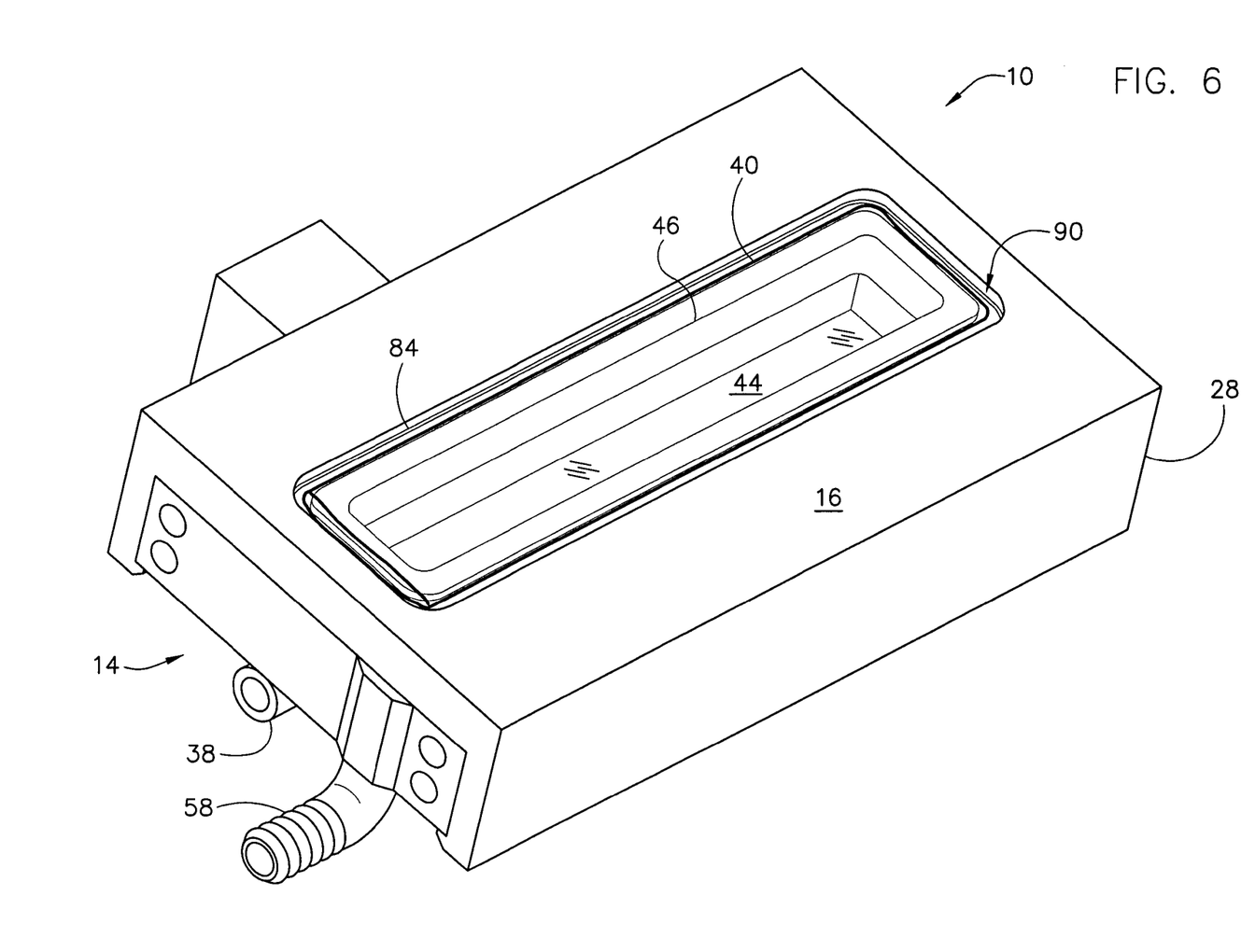
FIG. 6 is another perspective of the probe.

As shown in FIG. 6, the base 28 and the membrane 40, supported in place by the insert 46, form a moat 90 between them. During operation of the probe, the coupling fluid 88 is delivered through the coupling fluid outlet 84 and to the moat 90. The moat 90 generally fills with coupling fluid 88 as the fluid is delivered through the coupling fluid outlet 84. Before and/or after the moat 90 is filled with coupling fluid 88, the coupling fluid flows over the coupling surface 44 of the spacer 56. The coupling fluid outlet 84 may be configured to facilitate contact between the coupling fluid 88 and the coupling surface 44. For example, the coupling fluid outlet 84 may be configured so coupling fluid 88 exits the outlet at an angle between about vertically downward (i.e., 90° with the contact surface 16) and horizontally inward in a general direction of the spacer 56 to facilitate contact between the coupling fluid and the coupling surface 44 during operation of the probe. In a particular embodiment, the coupling fluid outlet 84 is configured so coupling fluid 88 exits the outlet at an angle between about 90° with the contact surface 16 and about 20° with the contact surface in a general direction of the spacer 56. Although other coupling fluids 88 may be used without departing from the scope of the present invention, in one embodiment the coupling fluid is water.

During operation of the probe 10, coupling fluid 88 delivered to the recess 74 and against the coupling surface 44 of the spacer 56 tends to adhere to and maintain contact with the coupling surface due to tension between the coupling fluid and the coupling surface. The coupling fluid 88 adhering to the coupling surface 44 forms a thin fluid film 92. In one embodiment, a thickness 94 of the film 92 is generally the same as the depth 76 of the recess. The fluid film 92 couples the spacer 56 to the part 12 when the probe 10 is used to examine the part. As will be appreciated by those skilled in the art, the coupling fluid film 92 facilitates transition of ultrasonic signals 96 (shown in FIG. 2) between the spacer 56 and the part 12. As shown in FIG. 3, some of the coupling fluid 88 from the film 92 stays with the part 12 as the probe 10 moves along the part. This residual fluid 98 is replaced in the recess 74 by additional coupling fluid 88 channeled to the recess through the coupling fluid outlet 84. The coupling fluid 88 can be fed to the recess 74 continuously or intermittently and at various rates without departing from the scope of the present invention. Feeding coupling fluid 88 to the recess 74 removes the need for external devices, such as spray bottles, to create the coupling between the spacer 56 and the part 12.

Due to its fluid nature, the film 92 generally connects a contact or upper surface 100 of the part 12 to the spacer 56 uninterrupted across the coupling surface 44 of the spacer. As shown in FIG. 3, the generally continuous fluid connection between the spacer 56 and the part 12 will remain intact even when the upper surface 100 of the part 12 has small protrusions 102 and/or small depressions 104. When the probe 10 is moved over a small protrusion 102 in the part surface 100, the film 92 deforms around the protrusion. When the probe 10 is moved over a small depression 104 in the part surface 100, the film 92 extends into the depression to fill it. In these ways, the fluid film 92 maintains a generally continuous connection between the spacer 56 and the part 12 despite discontinuities in the part surface 100. Further, the flexible membrane 40 can deform in response to the probe 10 encountering a part surface discontinuity 102, 104 and/or be actively adjusted to accommodate such discontinuities. For example, chamber 52 pressure can be decreased by the user or controller by decreasing flow into the chamber and/or increasing flow from the chamber so the membrane 40 flexes to its concave position 80. When the membrane 40 is in the concave position, the probe 10 can better accommodate part surface 100 protrusions 102 that become disposed in the recess 74. Also, the chamber 82 pressure can be increased by the user or controller by increasing flow into the chamber and/or decreasing flow from the chamber so the membrane 40 flexes to its convex position 78. When the membrane 40 is in the convex position, the probe 10 can better accommodate part surface 100 depressions 104 that the spacer 56 may move over. Particularly, the membrane 40 in the convex position 78 will apply a greater force toward the film 92 and the part 12 compared to an unflexed membrane so the film will more likely fill small depressions 104 and, thereby, keep unwanted air pockets from forming in the depressions between the probe 10 and the part.

The fluid film 92 will also remain in the recess 74 and against a substantial entirety of the coupling surface 44 of the spacer 56 when the probe 10 is moved over an edge 106 of the part 12. That is, because of its thinness and associated fluid dynamics, the film 92 maintains its general shape and position within the recess 74 and against the coupling surface 44 despite the probe 10 being moved to a position where the part 12 does not completely underlie the recess and film. The edge 106 can be an edge at an end of the part 12, as shown in FIG. 3, or an edge of a large void in the part surface 100. Maintaining the coupling fluid 88 throughout the recess 74 when the probe 10 crosses the edge 106 is important for determining part 12 characteristics adjacent the edge. If the coupling fluid 88 did not remain in the recess 74 when the probe 10 crossed the edge 106, the transducer 32 would receive mixed signals about exactly what underlies the probe near and at the edge. That is, many of the ultrasonic signals 96 leaving the transducer 32 would get scrambled in the coupling fluid 88 exiting the recess 74 and flowing over the edge 106 and the signals that do get reflected back to the transducer would not be sufficient to allow the user to accurately determine characteristics of the part 12 at and near the edge.

Further, loss of coupling fluid 88 from the film 92 beyond the edge 106 could result in losses of coupling fluid from the film at locations of the probe 10 adjacent the edge under which the part 12 still lies. Such additional coupling fluid 88 loss adds to the inaccurate reflected signals the transducer will measure. For example, as described in the Background of the Invention Section above, it is difficult to distinguish whether a signal reflected back to the transducer 32 from air below the probe indicates the signal was reflected from air beneath the probe beyond a part 12 edge 106 or air caused by a lack of coupling fluid between the probe and the part because the coupling fluid there flowed over the edge. On the other hand, when the fluid film 92 is maintained in the recess 74 continuously across the coupling surface 44 of the spacer 56 whether the probe 10 is positioned partly or completely over the part 12, the generally uniform coupling layer beneath the spacer allows the controller to better interpret the signals returned to the transducer 32. The controller will know whether changes in the quality and/or timing of returned signals result from changes in part 12 characteristics or a part edge 106. When the part 12 does not underlie a portion of the recess 74, the ultrasonic signals 96 transmitted from the transducer 32 and through the spacer 56 and film 92 will reflect from air 108 (shown in FIG. 3) below the film back to the transducer in a generally uniform manner due to the generally uniform shape of the film. More uniform reflected signals provide a more accurate indication of a shape and location of the part 12 including its edge 106.

The spacer 56 is positioned between the transducer 32 and the contact surface 16 for spacing the transducer from the part 12 when being examined. The materials and size of the spacer 56 control a manner in which the ultrasonic signals 96 are transmitted between the transducer 32 and the part 12. The spacer 56 is made of materials and sized so unwanted ultrasonic signals, such as signals 110 (shown in FIG. 2) reflected from unwanted air bubbles 70 in the spacer 56, are not confused with the signals 96 transmitted through the part 12 and back to the transducer 32 as intended. To avoid such confusion, the controller must be able to distinguish between signals 112 returning to the transducer 32 as intended and signals 110, 114, 116, 118, 120, 122 reflected back to the transducer in other ways.

As described above, the probe 10 may be used to determine characteristics of the part 12, including size, shape, and interior imperfections. For example, the probe 10 may be used to determine qualities of a lower surface 124 of the part 12, by transmitting ultrasonic signals 96 through the spacer 56 and into the part. Properly transmitted signals 112 reflect back toward the transducer 32 from the lower surface 124 of the part 12 as the signals encounter air 126 adjacent that surface. The reflected signals 112 propagate back through the part 12, the coupling film 92, and the spacer 56 and to the transducer 32. The controller determines characteristics of the part 12 based on a timing and/or strength of the returned signals 112. The controller may also consider a location at which a reflected signal 112 returns to the transducer 32. Signals 110, 114, 116, 118, 120, 122 reflected back to the transducer 32 in unintended ways muddle transducer feedback, which interferes with the ability of the controller to accurately determine part 12 characteristics.

Signals reflected back to the transducer 32 in unintended ways include signals 110 reflected at unwanted air bubbles 70 that may be created in the delay fluid 54, signals 114 reflected at the coupling surface 44 of the spacer 56, signals 116 reflected between the coupling film 92 and the part 12, signals 118 reflected at the lower surface 124 of the part 12 as intended but then reflected back down between the coupling film and the part, signals 120 reflected at the lower surface of the part as intended but then reflected back down at the coupling surface, and signals 122 that echo or get temporarily trapped between surfaces 44, 100, 124. For a part 12 having a thickness 128 in a known range, the controller can be programmed to expect the intended reflected signals 112 to return to the transducer 32 at a particular time and strength. The controller can distinguish between intended reflected signals 112 and unintended reflected signals 110, 114, 116, 118, 120, 122 based on the timing and/or strength of the returned signals. The controller can be programmed to determine that a slight deviation from the expected time and/or strength of a returned signal is due to a small change in the shape of the part 12 or a small error in the part. The controller can be programmed to conclude that a large deviation from an expected time and strength indicates either a large change in part 12 shape, a large error in the part, or that the signal is an unintended reflection 110, 114, 116, 118, 120, 122. By being able to distinguish between intended reflected signals 112 and unintended reflected signals 110, 114, 116, 118, 120, 122, the controller can better consider the intended reflected signals to accurately determine part 12 characteristics.

The spacer 56 is sized and made of materials that enable the controller to better distinguish intended reflected signals 112 from unintended reflected signals 110, 114, 116, 118, 120, 122. The controller considers the speed at which signals 96 are expected to travel through the spacer 56 and the part 12 and back to the transducer 32 for particular spacer materials and part materials and a particular spacer size and part size. The controller may also consider dimensions and a type of the coupling fluid 88 used. Various spacer 56 sizes and materials can be used to optimize the ability of the controller to distinguish the intended return signals 112 from the unintended return signals 110, 114, 116, 118, 120, 122 for a given part 12 size and material. The probe 10 can be used with any one of multiple differently sized spacers 56. Each of the differently sized spacers 56 can correspond to a part 12 having a thickness 128 in a particular range. For example, in one embodiment, a spacer having a height 130 (shown in FIG. 3) of between about 0.6 inch and about 0.7 inch when the membrane 40 is unflexed is used when the thickness 128 of the part 12 being examined is between about 0.08 inch and about 0.70 inch. Although the probe 10 may be used with a spacer 56 outside of a size range determined to correspond best to the particular part 12 being examined, using the preferred spacer size facilitates the ability of the controller to distinguish between wanted return signals 112 and unwanted return signals 110, 114, 116, 118, 120, 122 and more accurately determine part qualities.

Along with the size of the spacer 56, the materials of the spacer affect propagation of signals 96 through the spacer. Thus, the size and materials of the spacer 56 are considered in selecting the proper spacer to use for a particular application. Because the spacer 56 is made of multiple parts (i.e., the delay fluid 54 and the membrane 40), spacer qualities will generally not be completely homogenous. For design purposes, many of the qualities of the delay fluid 54 can be attributed to the entire spacer 56 because the delay fluid comprises a vast majority of the spacer and almost all of the spacer taken along a vertical line of the probe 10. For example, the sonic velocity of the delay fluid 54 can generally be considered as the sonic velocity of the spacer 56. Although the spacer 56 may have other sonic velocities without departing from the scope of the present invention, in one embodiment the spacer has a sonic velocity of between about 1,200 cm/ms and about 1,300 cm/ms. In one particular embodiment, the spacer has a sonic velocity of about 1,270 cm/ms or about the sonic velocity of water.

The probe 10 may also include an encoder 132 (shown in FIGS. 1 and 2) mounted on the body 14. The encoder 132 is used to measure probe 10 displacement with respect to the part 12 when the probe is moved along the upper part surface 100. The controller can use the displacement measurements from the encoder 132 in various ways. In one embodiment, the controller can use the displacement measurements to create a map (not shown) of the part 12 including part characteristics determined by the transducer 32 at the various positions identified by the encoder 132. The controller may also compare measured part 12 characteristics to specification characteristics to determine how true a part is to design. For example, a controller may be programmed to expect the undersurface 124 of the part 12 to have an indentation 134 (shown in FIG. 3) and a projection 136 at respective distances from a starting edge (not shown) of the part. Thus, when the probe 10 moves over the indentation 134 and/or the projection 136, the controller will expect the intended return signals 112 to return accordingly, such as at an expected timing and signal strength. The encoder 132 can also be used to determine a rate of probe 10 movement with respect to the part 12. This rate can be used to control, for example, a rate at which coupling fluid 88 is fed to the recess 74.

During use, the delay fluid inlet 58 and coupling fluid inlet 82 are connected to the same or different fluid sources (not shown), such as sources of water. If the controller is an external controller, the probe 10 is connected to the controller by way of the control port 38. The contact surface 16 of the probe 10 body 14 is positioned in contact with the contact surface 100 of the part 12. Before or after the probe 10 is placed in contact with the part 12, delay fluid 54 is delivered from the delay fluid source to the chamber 52 by way of the delay fluid inlet 58, the delay fluid feed channel 62, and the chamber inlet 60. Also before or after the probe 10 is placed in contact with the part 12, the coupling fluid 88 is delivered from the coupling fluid source to the recess 74 by way of the coupling fluid inlet 82, the coupling fluid channel 86, and the coupling fluid outlet 84. The delay fluid 54 and the coupling fluid 88 may be delivered continuously or intermittently to the chamber 52 and recess 74, respectively, during operation of the probe 10.

Delivering the delay fluid 54 to the chamber 52 may include controlling a rate at which the delay fluid passes into the chamber and/or a rate at which the delay fluid passes out of the chamber. Rates can be controlled manually or automatically by way of valves (not shown) that are external or internal to the probe 10. The flow rates through the chamber inlet and outlet 60, 66 can be adjusted to increase or decrease the rate of flow through the chamber 52 or to change the chamber pressure. For example, the mass flow rate of delay fluid 54 passing through the chamber 52 can be increase or decreased by increasing or decreasing flow rates through both the chamber inlet and outlet 60, 66. When a ratio of the flow rate of delay fluid 54 passing through the fluid inlet 60 and the fluid outlet 66 is increased (e.g., by increasing the rate of fluid passing through the inlet and decreasing or not changing the rate of fluid passing through the outlet), chamber 52 pressure is increased. When a ratio of the flow rate of delay fluid 54 passing through the fluid inlet 60 and the fluid outlet 66 is decreased (e.g., by decreasing the rate of fluid passing through the inlet and not changing the rate of fluid passing through the outlet), chamber 52 pressure is decreased.

When the pressure in the chamber 52 is raised above a predetermined amount, the flexible membrane 40 will flex convexly, generally in proportion to an amount of pressure increase above the predetermined amount. When the pressure in the chamber 52 is lowered below a predetermined amount, the flexible membrane 40 will flex concavely, generally in proportion to an amount of pressure increase above the predetermined amount. Deforming the membrane 40 may be performed while the probe 10 is being used to examine the part 12. The membrane 40 may be flexed outward or inward to accommodate a protrusion 102 or depression 104 in the contact surface 100 of the part 12 to ensure the coupling fluid 88 connects the spacer 56 to the part 12 across substantially all of the coupling surface 44 of the spacer.

Delivering the coupling fluid 88 to the recess 74 may include controlling a rate at which the coupling fluid passes through the coupling fluid channel 86 and out of the coupling fluid outlet 84. The coupling fluid 88 delivered to the recess 74 forms the thin film 92 as it adheres to the coupling surface 44 of the spacer 56 due to surface tension. The film 92 is maintained across the coupling surface 44 whether the probe 10 is being moved over a smooth surface, protrusions 102, depressions 104, and/or an edge 106 of the part 12 so a portion of the spacer 56 is positioned above the part and a portion of the spacer is not positioned above the part.

Using the probe 10 further includes producing signals 96 using the transducer 32. The signals 96 are transmitted from the transducer 32, through the spacer 56, through the thin coupling film 92, and into the part 12 and reflected back through the part. The probe 10 is moved along the part 12 while the coupling fluid 88 is delivered to the recess 74 and the ultrasonic signals 96 are transmitted. The signals 96 produced by the transducer 32 that are reflected back through the film 92 and the spacer 56 and to the transducer from the part 12 are sensed by the transducer. The controller determines characteristics of the part 12 based on the signals sensed by the transducer 32. Determining part 12 characteristics may include determining a location and/or dimensions of an indentation 134, a projection 136, and/or an edge 106 of the part 12. Although the probe 10 may be moved along the part surface 100 at other rates while determining part characteristics using the transducer 32, in one embodiment the probe is moved along the part surface at a rate of between about 5 inches/second and about 16 inches/second while determining part characteristics using the transducer.

Probe 10 use may also include measuring displacement of the probe using the encoder 132 while the probe is moved along the part surface 100. The controller can consider the location of the probe 10 on the part 12, as determined by the encoder 132, in determining part characteristics. For example, as described above, the controller can use the displacement measurements from the encoder 132 to create a map (not shown) of the part 12 and may compare measured part characteristics to specification part shapes and/or dimensions. Further, the encoder 132 can be used to determine a rate at which the probe 10 is moved along the part 12 surface 100. The probe 10 movement rate can be used to control, for example, the rate at which coupling fluid 88 is fed to the recess 74. To more accurately determine part 12 characteristics, the spacer 56 materials and size are selected so intended reflected signals 112 are not confused with unintended reflected signals 110, 114, 116, 118, 120, 122.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An ultrasonic probe for examining an item, the probe comprising:
 a body having a contact surface;
 a flexible membrane secured to one end of the body, the flexible membrane having a coupling surface;
 an ultrasonic transducer attached to the body and spaced from the flexible membrane, a chamber formed by the membrane, the body and the transducer; and
 a fluid outlet positioned adjacent the coupling surface of the membrane for delivering coupling fluid to the coupling surface as a film so that the coupling fluid tends to maintain contact with the membrane due to surface tension after the fluid is delivered through the outlet;

wherein pressure in the chamber is varied to cause the membrane to flex to accommodate a surface of the item.

2. The ultrasonic probe as set forth in claim 1 further comprising a delay fluid within the chamber, wherein chamber pressure is controlled by flow rate of the delay fluid.

3. The ultrasonic probe as set forth in claim 2 wherein said membrane flexes inward and outward from an unflexed position; and the coupling surface of the membrane is offset from the contact surface when the membrane is in the unflexed position and an inwardly flexed position forming a recess through which said coupling fluid film moves during operation of the probe.

4. The ultrasonic probe as set forth in claim 1 wherein said coupling surface of the membrane is offset from the contact surface of the body to form a recess through which said coupling fluid film moves during operation of the probe.

5. The ultrasonic probe as set forth in claim 4 wherein said fluid outlet includes a single port distributed around said recess.

6. The ultrasonic probe as set forth in claim 1 wherein the body comprises a polymer.

7. The ultrasonic probe as set forth in claim 1 further comprising a controller for controlling pressure in the chamber in response to changes on the surface of the item.

8. The ultrasonic probe as set forth in claim 1 wherein the transducer includes an array of elements, each element including a crystal that oscillates to create ultrasonic signals with which the item is examined during operation of the probe.

9. The ultrasonic probe as set forth in claim 1 further comprising an encoder mounted on the body for measuring displacement of the probe as it moves along a surface of the item during operation of the probe.

10. The ultrasonic probe as set forth in claim 1 wherein the coupling fluid passes through said outlet at an angle of between about 90° and about 20° with the contact surface in a general direction of the membrane to facilitate contact between the coupling fluid and the coupling surface of the membrane during operation of the probe.

11. The ultrasonic probe as set forth in claim 1, wherein the membrane is attached to the probe body such that the membrane flexes concavely and convexly.

12. The ultrasonic probe as set forth in claim 1, wherein in the variations in chamber pressure do not cause the probe body to flex.

13. An ultrasonic probe for examining an item, the probe comprising:

a body having a contact surface;

a flexible membrane secured to one end of the body, the flexible membrane having a coupling surface that is offset from the contact surface; and an ultrasonic transducer attached to the body and spaced from the flexible membrane, a chamber formed by the membrane, the body and the transducer; and wherein pressure in the chamber is varied to cause the membrane, but not the body, to flex to accommodate a surface of the item.

* * * * *